US011415715B2

(12) United States Patent
Iwakiri (10) Patent No.: US 11,415,715 B2
(45) Date of Patent: *Aug. 16, 2022

(54) RADIATION IMAGE CAPTURING APPARATUS

(71) Applicant: FUJIFILM Corporation, Tokyo (JP)

(72) Inventor: Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 57 days.

This patent is subject to a terminal disclaimer.

(21) Appl. No.: 17/029,697

(22) Filed: Sep. 23, 2020

(65) Prior Publication Data

US 2021/0003723 A1    Jan. 7, 2021

Related U.S. Application Data

(63) Continuation of application No. PCT/JP2019/007504, filed on Feb. 27, 2019.

(30) Foreign Application Priority Data

Mar. 26, 2018   (JP) .............................. JP2018-058964

(51) Int. Cl.
  *G01T 1/29*   (2006.01)
  *G01T 1/17*   (2006.01)
  *G01T 1/20*   (2006.01)

(52) U.S. Cl.
  CPC .............. *G01T 1/2978* (2013.01); *G01T 1/17* (2013.01); *G01T 1/20188* (2020.05)

(58) Field of Classification Search
  CPC ...... G01T 1/2978; G01T 1/20188; G01T 1/17
  See application file for complete search history.

(56) References Cited

U.S. PATENT DOCUMENTS

| 2003/0031296 A1* | 2/2003 | Hoheisel | ............... | G01T 1/2018 |
| | | | | 378/98.8 |
| 2008/0287747 A1* | 11/2008 | Mestrovic | .............. | H05K 1/147 |
| | | | | 600/300 |
| 2010/0193691 A1 | 8/2010 | Ishii et al. | | |

(Continued)

FOREIGN PATENT DOCUMENTS

| JP | 2003070776 A | 3/2003 |
| JP | 2008122116 A | 5/2008 |

(Continued)

OTHER PUBLICATIONS

Adachi—WO-2010070735-A1—Google Patents English obtained Jan. 13, 2022 (Year: 2022).*

(Continued)

*Primary Examiner* — David P Porta
*Assistant Examiner* — Jeremy S Valentiner
(74) *Attorney, Agent, or Firm* — Studebaker & Brackett PC (57) ABSTRACT

A radiation image capturing apparatus including a sensor substrate including a flexible base material and a plurality of pixels accumulating electric charges generated in accordance with radiation, a flexible first cable of which one end is electrically connected to the sensor substrate, and a flexible first circuit substrate that is electrically connected to the other end of the first cable and in which a first circuit unit driven in a case of reading out the electric charges accumulated in the plurality of pixels is mounted is provided.

19 Claims, 6 Drawing Sheets

(56) References Cited

U.S. PATENT DOCUMENTS

2014/0312238 A1* 10/2014 Liu ..................... G01T 1/1618
                                                    250/363.03
2016/0170038 A1*  6/2016 Yu ........................... G01T 1/17
                                                    250/394
2016/0341689 A1* 11/2016 Guenschel ......... G01N 27/4078

FOREIGN PATENT DOCUMENTS

| JP | 2009-133837 A | 6/2009 | |
|---|---|---|---|
| JP | 2010085266 A | 4/2010 | |
| JP | 2011075327 A | 4/2011 | |
| JP | 2012133315 A | 7/2012 | |
| WO | 2010070735 A1 | 6/2010 | |
| WO | WO-2010070735 A1 * | 6/2010 | ......... H01L 27/1218 |

OTHER PUBLICATIONS

International Search Report issued in PCT/JP2019/007504; dated May 14, 2019.
International Preliminary Report on Patentability and Written Opinion issued in PCT/JP2019/007504; dated Sep. 29, 2020.

* cited by examiner

RADIATION IMAGE CAPTURING APPARATUS

CROSS-REFERENCE TO RELATED APPLICATIONS

This application is a continuation application of International Application No. PCT/JP2019/007504, filed on Feb. 27, 2019, which is incorporated herein by reference in its entirety. Further, this application claims priority from Japanese Patent Application No. 2018-058964, filed on Mar. 26, 2018, the disclosure of which is incorporated by reference herein.

BACKGROUND

Technical Field

The present disclosure relates to a radiation image capturing apparatus.

Related Art

In the related art, a radiation image capturing apparatus that performs radiation imaging for the purpose of medical diagnosis has been known. In such a radiation image capturing apparatus, a radiation detector for detecting radiation transmitted through a subject and generating a radiation image is used.

A radiation detector comprising a sensor substrate in which a plurality of pixels accumulating electric charges generated in accordance with radiation are disposed is present. In such a radiation detector, by electrically connecting a circuit unit disposed outside the sensor substrate to the sensor substrate, the electric charges accumulated in each pixel are read out by driving the circuit unit. Connection between the sensor substrate and the circuit unit is performed by electrically connecting a cable such as a flexible cable to a base material of the sensor substrate.

In addition, a radiation detector using a flexible base material in the sensor substrate has been known (for example, refer to WO2010/070735). By using the flexible base material, for example, the weight of the radiation image capturing apparatus (radiation detector) can be reduced, and imaging of the subject may be facilitated.

A method called a lamination method has been known as an example of a method of manufacturing the radiation detector using the flexible base material in the sensor substrate. In the lamination method, a sheet as the flexible base material is bonded to a support such as a glass substrate. Furthermore, the sensor substrate and a conversion layer are formed. Then, the sensor substrate in which the conversion layer is formed is stripped from the support by mechanical stripping.

In the case of stripping the sensor substrate from the support by mechanical stripping, for example, any side of the outer edge of the sensor substrate is set as a starting point of stripping, and the sensor substrate is gradually peeled from the support from the side as the starting point to the opposite side.

The mechanical stripping may be performed in a state where a circuit substrate on which the circuit unit disposed outside is mounted is electrically connected to the sensor substrate through a cable. In the case of performing the mechanical stripping in such a state, the sensor substrate is bent. Thus, the circuit substrate is also bent in accordance with bending of the sensor substrate, and a problem such as damage to the circuit substrate or the circuit unit mounted on the circuit substrate may arise.

SUMMARY

The present disclosure provides a radiation image capturing apparatus capable of suppressing an effect exerted on a first circuit unit in a state where a first circuit substrate is electrically connected to a sensor substrate through a first cable, compared to a case where the first circuit substrate is a non-flexible substrate.

A first aspect of the present disclosure is a radiation image capturing apparatus comprising a sensor substrate including a flexible base material and a plurality of pixels accumulating electric charges generated in accordance with radiation, a flexible first cable of which one end is electrically connected to the sensor substrate, and a flexible first circuit substrate that is electrically connected to the other end of the first cable and in which a first circuit unit driven in a case of reading out the electric charges accumulated in the plurality of pixels is mounted.

A second aspect of the present disclosure is such that in the first aspect, the first cable may be connected to a first side of the sensor substrate, and the radiation image capturing apparatus may further comprise a flexible second cable of which one end is electrically connected to a second side intersecting with the first side of the sensor substrate, and a non-flexible second circuit substrate that is electrically connected to the other end of the second cable and in which a second circuit unit which is different from the first circuit unit and is driven in a case of reading out the electric charges accumulated in the plurality of pixels is mounted.

A third aspect of the present disclosure is such that in the second aspect, the second circuit unit may include a circuit of a signal processing unit into which an electric signal corresponding to the electric charges accumulated in the plurality of pixels is input and that generates and outputs image data corresponding to the input electric signal.

A fourth aspect of the present disclosure is such that in the first aspect or the second aspect, the second circuit substrate may include a connector to which the second cable is electrically connected.

A fifth aspect of the present disclosure is such that in the first aspect, the first circuit unit may include a circuit of a driving unit that reads out the electric charges from the plurality of pixels.

A sixth aspect of the present disclosure is such that in the first aspect, the first circuit substrate may have a flexible region and a non-flexible region that are lined up in a direction intersecting with a connection direction in which the sensor substrate, the first cable, and the first circuit substrate are connected.

A seventh aspect of the present disclosure is such that in the sixth aspect, the first circuit unit may be mounted in the non-flexible region.

An eighth aspect of the present disclosure is such that in the first aspect, the circuit of the driving unit reading out the electric charges from the plurality of pixels may be mounted in the first cable, and a power supply line supplying power of a power supply to the circuit of the driving unit may be disposed in the first circuit substrate and the first cable.

A ninth aspect of the present disclosure is such that in the first aspect, a circuit of a driving unit reading out the electric charges from the plurality of pixels may be mounted in the first cable, and a power supply line supplying power of a power supply to the circuit of the driving unit may not be disposed in the sensor substrate.

A tenth aspect of the present disclosure is such that in the eighth aspect or the ninth aspect, the circuit of the driving unit reading out the electric charges from the plurality of pixels may be mounted in the first cable, and a signal line through which a signal for driving the circuit of the driving unit flows may be disposed in the sensor substrate and the first cable.

An eleventh aspect of the present disclosure is such that in any one of the first aspect to the tenth aspect, the first cable may be electrically connected to the first circuit substrate by thermocompression.

A twelfth aspect of the present disclosure is such that in any one of the first aspect to the eleventh aspect, the first cable may be electrically connected to the sensor substrate by thermocompression.

According to the first aspect of the present disclosure, an effect exerted on the first circuit unit in a state where the first circuit substrate is electrically connected to the sensor substrate through the first cable can be suppressed compared to a case where the first circuit substrate is a non-flexible substrate.

According to the second aspect of the present disclosure, electrical interference in the second circuit unit can be suppressed compared to a case where the second circuit substrate is a flexible substrate.

According to the third aspect of the present disclosure, electrical interference in the signal processing unit can be suppressed compared to a case where the signal processing unit is included in the first circuit unit.

According to the fourth aspect of the present disclosure, reworking of the second cable can be easily performed compared to a case where the second circuit substrate does not comprise the connector.

According to the fifth aspect of the present disclosure, even in a case where the first circuit substrate has flexibility, an effect of electrical interference in the first circuit unit can be suppressed compared to a case where the first circuit unit includes a circuit in addition to the circuit of the driving unit.

According to the sixth aspect of the present disclosure, the sensor substrate can be easily bent compared to a case where the first circuit substrate has the flexible region and the non-flexible region lined up in the connection direction.

According to the seventh aspect of the present disclosure, damage to the first circuit unit can be suppressed compared to a case where the first circuit unit is mounted in the flexible region.

According to the eighth aspect of the present disclosure, a resistance value in the sensor substrate can be decreased compared to a case where the power supply line supplying the power of the power supply to the circuit of the driving unit is disposed in addition to the first circuit substrate and the first cable.

According to the ninth aspect of the present disclosure, the resistance value in the sensor substrate can be decreased compared to a case where the power supply line supplying the power of the power supply to the circuit of the driving unit is disposed in the sensor substrate.

According to the tenth aspect of the present disclosure, the signal line can be arranged at a position separated from the power supply line compared to a case where the signal line through which the signal for driving the circuit of the driving unit flows is disposed in other than the sensor substrate.

According to the eleventh aspect of the present disclosure, the sensor substrate can be easily bent in a state where the first cable is connected to the first circuit substrate, compared to a case where the first cable is electrically connected to the first circuit substrate through the connector.

According to the twelfth aspect of the present disclosure, the sensor substrate can be easily bent in a state where the first cable is connected, compared to a case where the first cable is electrically connected to the sensor substrate through the connector.

DESCRIPTION OF EMBODIMENTS

Hereinafter, exemplary embodiments of the present disclosure will be described in detail with reference to the drawings. The present exemplary embodiment does not limit the present disclosure.

First Exemplary Embodiment

A radiation image capturing apparatus of the present exemplary embodiment has a function of capturing a radiation image of an imaging target by detecting radiation transmitted through a subject which is the imaging target and outputting image information representing the radiation image of the subject.

Figure 1:
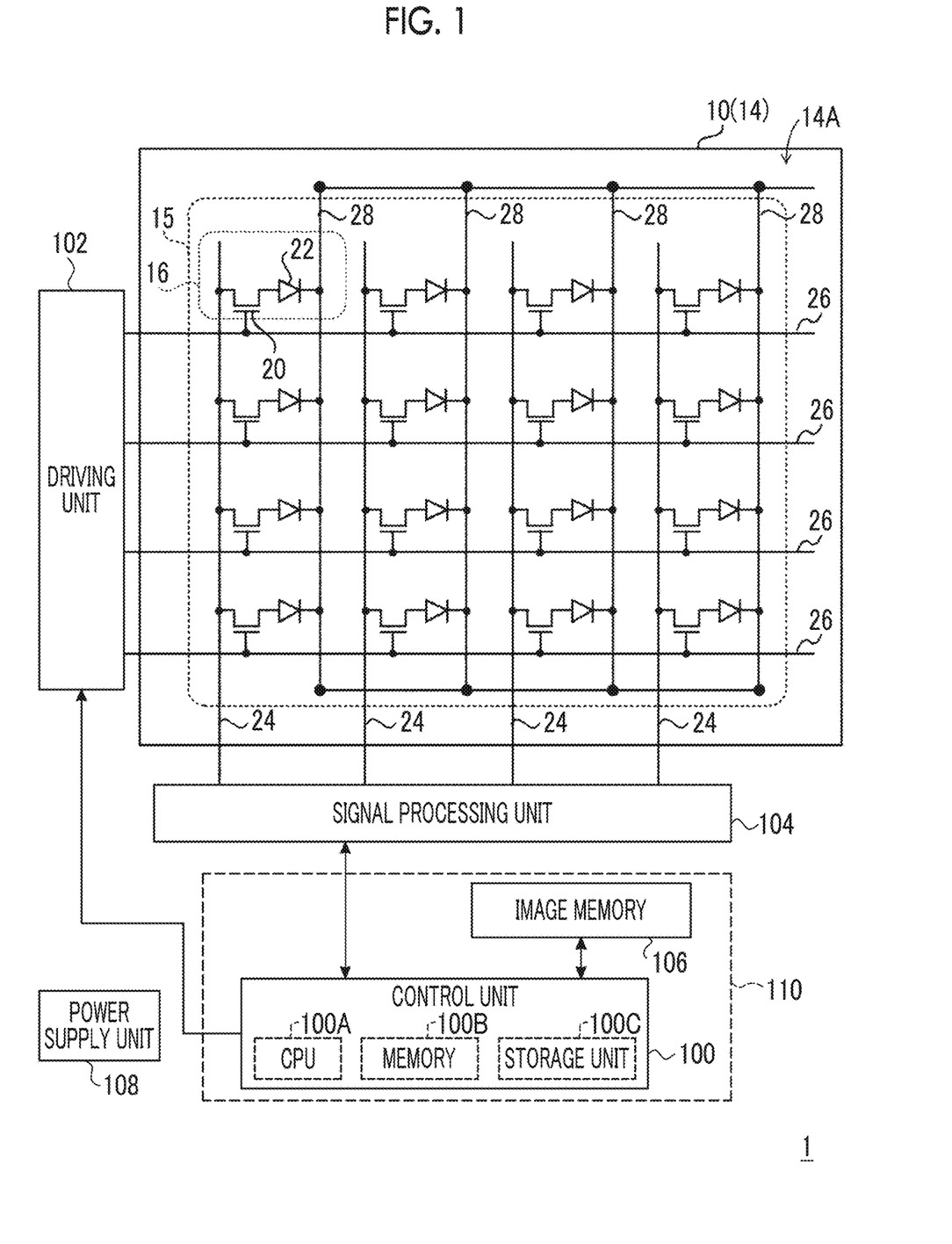
FIG. 1 is a block diagram illustrating one example of a main configuration of an electric system in a radiation image capturing apparatus of a first exemplary embodiment.

First, a summary of one example of a configuration of an electric system in the radiation image capturing apparatus of the present exemplary embodiment will be described with reference to FIG. 1. FIG. 1 is a block diagram illustrating one example of a main configuration of an electric system in a radiation image capturing apparatus of a first exemplary embodiment.

A radiation detector 10 comprises a sensor substrate 12 (refer to FIG. 2) and a conversion layer (refer to FIG. 2) that converts radiation into light. The sensor substrate 12 comprises a flexible base material 14 and a plurality of pixels 16 disposed on a first surface 14A of the base material 14. Hereinafter, the plurality of pixels 16 may be simply referred to as the "pixels 16".

As illustrated in FIG. 1, each pixel 16 of the present exemplary embodiment comprises a sensor unit 22 that generates electric charges in accordance with the light converted by the conversion layer and accumulates the electric charges, and a switching element 20 that reads out the electric charges accumulated in the sensor unit 22. In the present exemplary embodiment, for example, a thin film transistor (TFT) is used as the switching element 20. Thus, hereinafter, the switching element 20 will be referred to as the "TFT 20". In the present exemplary embodiment, a layer in which the sensor unit 22 and the TFT 20 are formed and furthermore, the pixels 16 are formed is disposed on the first surface 14A of the base material 14 as a flattened layer. Hereinafter, the layer in which the pixels 16 are formed may be referred to as the "pixels 16" for convenience of description.

The pixels 16 are two-dimensionally arranged in an active area 15 of the sensor substrate 12 in one direction (a scanning wire direction corresponding to a horizontal direction in FIG. 1; hereinafter, referred to as a "row direction") and a direction (a signal wire direction corresponding to a vertical direction in FIG. 1; hereinafter, referred to as a "column direction") intersecting with the row direction. While arrangement of the pixels 16 is illustrated in a simplified manner in FIG. 1, for example, 1024×1024 pixels 16 are arranged in the row direction and the column direction.

In addition, in the radiation detector 10, a plurality of scanning wires 26 that are comprised for each row of the pixels 16 for controlling a switching state (ON and OFF) of the TFT 20 and a plurality of signal wires 24 that are comprised for each column of the pixels 16 and to which the electric charges accumulated in the sensor unit 22 are read out are disposed in intersection with each other. Each of the plurality of scanning wires 26 is electrically connected to a driving unit 102. A control unit 100, described later, is connected to the driving unit 102. The driving unit 102 outputs a drive signal in accordance with a control signal output from the control unit 100. The driving signal output from the driving unit 102 for controlling the switching state by driving the TFT 20 flows through each of the plurality of scanning wires 26. In addition, by electrically connecting each of the plurality of signal wires 24 to a signal processing unit 104, the electric charges read out from each pixel 16 are output to the signal processing unit 104 as an electric signal. The signal processing unit 104 generates and outputs image data corresponding to the input electric signal.

The control unit 100, described later, is connected to the signal processing unit 104, and the image data output from the signal processing unit 104 is sequentially output to the control unit 100. An image memory 106 is connected to the control unit 100, and the image data sequentially output from the signal processing unit 104 is sequentially stored in the image memory 106 under control of the control unit 100. The image memory 106 has a storage capacity in which image data corresponding to a predetermined number of images can be stored. Each time the radiation image is captured, the image data obtained by imaging is sequentially stored in the image memory 106.

The control unit 100 comprises a central processing unit (CPU) 100A, a memory 100B including a read only memory (ROM), a random access memory (RAM), and the like, and a non-volatile storage unit 100C such as a flash memory. One example of the control unit 100 is exemplified by a microcomputer or the like. The control unit 100 controls the operation of the entire radiation image capturing apparatus 1.

In the radiation image capturing apparatus 1 of the present exemplary embodiment, the image memory 106, the control unit 100, and the like are formed in a control substrate 110.

In addition, a common wire 28 is disposed in the sensor unit 22 of each pixel 16 in a wire direction of the signal wire 24 in order to apply a bias voltage to each pixel 16. By electrically connecting the common wire 28 to a bias power supply (not illustrated) outside the sensor substrate 12, the bias voltage is applied to each pixel 16 from the bias power supply.

A power supply unit 108 supplies electric power to various elements and various circuits such as the control unit 100, the driving unit 102, the signal processing unit 104, the image memory 106, and the power supply unit 108. In FIG. 1, wires connecting the power supply unit 108 to various elements and various circuits are not illustrated in order to avoid complication.

Figure 2:
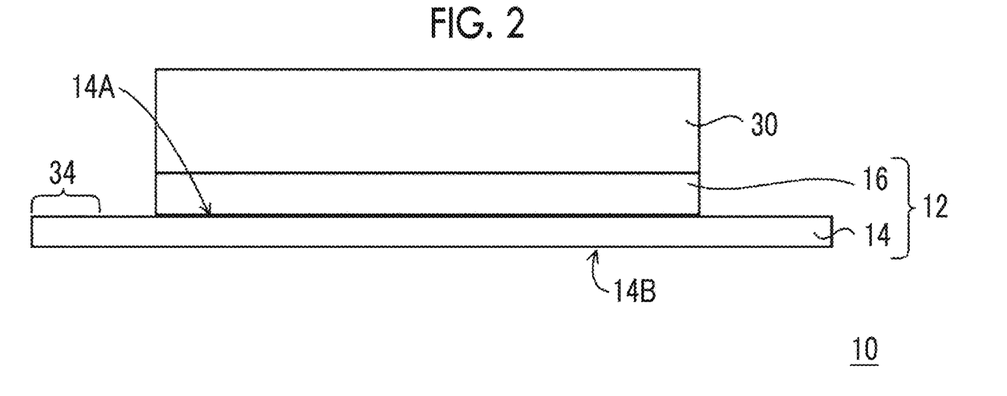
FIG. 2 is a cross-sectional view illustrating a summary of one example of a configuration of a radiation detector of the first exemplary embodiment.

The radiation detector 10 of the present exemplary embodiment will be further described in detail. FIG. 2 is a cross-sectional view illustrating a summary of one example of the radiation detector 10 of the present exemplary embodiment.

As illustrated in FIG. 2, the radiation detector 10 of the present exemplary embodiment comprises the sensor substrate 12 including the base material 14 and the pixels 16, and a conversion layer 30. The base material 14, the pixels 16, and the conversion layer 30 are disposed in this order. Hereinafter, a direction (up-down direction in FIG. 2) in which the base material 14, the pixels 16, and the conversion layer 30 are laminated will be referred to as a lamination direction.

The base material 14 is a resin sheet that has flexibility and includes plastic such as polyimide. A specific example of the base material 14 is exemplified by XENOMAX (registered trademark). The base material 14 is not limited to the resin sheet, provided that the base material 14 has desired flexibility. For example, the base material 14 may be a glass substrate or the like having a relatively small thickness. The thickness of the base material 14 may be a thickness in which desired flexibility is obtained depending on the hardness of the substance, the size (the area of the first surface 14A or a second surface 14B) of the sensor substrate 12, and the like. For example, in a case where the base material 14 is the resin sheet, the thickness may be 5 µm to 125 µm. Alternatively, for example, in a case where the base material 14 is the glass substrate, the base material 14 generally has flexibility in a case where the thickness is less than or equal to 0.1 mm in a size of 43 cm or less for one side. Thus, the thickness may be less than or equal to 0.1 mm.

As illustrated in FIG. 2, the plurality of pixels 16 are disposed in a partial region inside the first surface 14A of the base material 14. That is, in the sensor substrate 12 of the present exemplary embodiment, the pixels 16 are not disposed in an outer periphery portion of the first surface 14A of the base material 14. In the present exemplary embodiment, a region in which the pixels 16 are disposed on the first surface 14A of the base material 14 is set as the active area 15. In the present exemplary embodiment, for example, the pixels 16 are disposed on the first surface 14A of the base material 14 through an undercoat (not illustrated) using SiN or the like.

In addition, as illustrated in FIG. 2, the outer periphery of the first surface 14A of the base material 14 is set as a terminal region 34 in which a terminal electrically connected to the signal wire 24 or the scanning wire 26 is disposed.

In addition, as illustrated in FIG. 2, the conversion layer 30 covers the active area 15. In the present exemplary embodiment, a scintillator including cesium iodide (CsI) is used as one example of the conversion layer 30. For example, it is preferable that such a scintillator includes CsI:Tl (cesium iodide to which thallium is added) or CsI:Na (cesium iodide to which sodium is added) of which the light emission spectrum at the time of X ray irradiation is 400 nm to 700 nm. The light emission peak wavelength of CsI:Tl in a visible light spectrum is 565 nm.

In the present exemplary embodiment, the conversion layer 30 of CsI is directly formed on the sensor substrate 12 as columnar crystal using a vapor deposition method such as a vacuum evaporation method, a sputtering method, and a chemical vapor deposition (CVD) method. In this case, the side of the conversion layer 30 that is in contact with the pixels 16 is set as a base point side of the growth direction of the columnar crystal.

In a case where the conversion layer of CsI is directly formed on the sensor substrate 12 using the vapor deposition method, for example, a reflection layer (not illustrated) having a function of reflecting the light converted by the conversion layer 30 may be disposed on a surface on a side opposite to the side in contact with the sensor substrate 12. The reflection layer may directly disposed in the conversion layer 30 or may be disposed through an adhesive layer or the like. In this case, it is preferable to use an organic-based material as the material of the reflection layer. For example, it is preferable to use at least one of white polyethylene terephthalate (PET), $TiO_2$, $Al_2O_3$, foamed white PET, a polyester-based high reflection sheet, or specular reflection aluminum as the material. Particularly, it is preferable to use white PET as the material from the viewpoint of reflectance.

White PET is obtained by adding a white pigment such as $TiO_2$ or barium sulfate to PET. The polyester-based high reflection sheet is a sheet (film) having a multilayer structure in which a plurality of thin polyester sheets are stacked. Foamed white PET is white PET having a porous surface.

In the case of using the scintillator of CsI as the conversion layer 30, the conversion layer 30 can be formed in the sensor substrate 12 using a different method from the present exemplary embodiment. For example, the conversion layer 30 may be formed in the sensor substrate 12 by preparing an aluminum plate or the like on which CsI is vapor-deposited using the vapor deposition method and bonding the side of CsI not in contact with the aluminum plate to the pixels 16 of the sensor substrate 12 using an adhesive sheet or the like.

Furthermore, unlike the radiation detector 10 of the present exemplary embodiment, $Gd_2O_2S$:Tb (GOS) or the like may be used as the conversion layer 30 instead of CsI. In this case, for example, the conversion layer 30 can be formed in the sensor substrate 12 by preparing bonding of a sheet obtained by dispersing GOS in a binder of resin or the like to a support formed by white PET or the like using an adhesive layer or the like, and bonding a side of the GOS to which the support is not bonded to the pixels 16 of the sensor substrate 12 using an adhesive sheet or the like.

A protective film or an antistatic film that covers a part or the entirety of the radiation detector 10 or the conversion layer 30 or the like may be disposed. For example, a Parylene (registered trademark) film or an insulating sheet of polyethylene terephthalate or the like is exemplified as the protective film. In addition, for example, a sheet of Alupet (registered trademark) in which an insulating sheet (film) of polyethylene terephthalate or the like is laminated with aluminum by bonding an aluminum foil, or a film using an antistatic paint "Colcoat" (product name; manufactured by Colcoat Co., Ltd.) is exemplified as the antistatic film.

Figure 3:
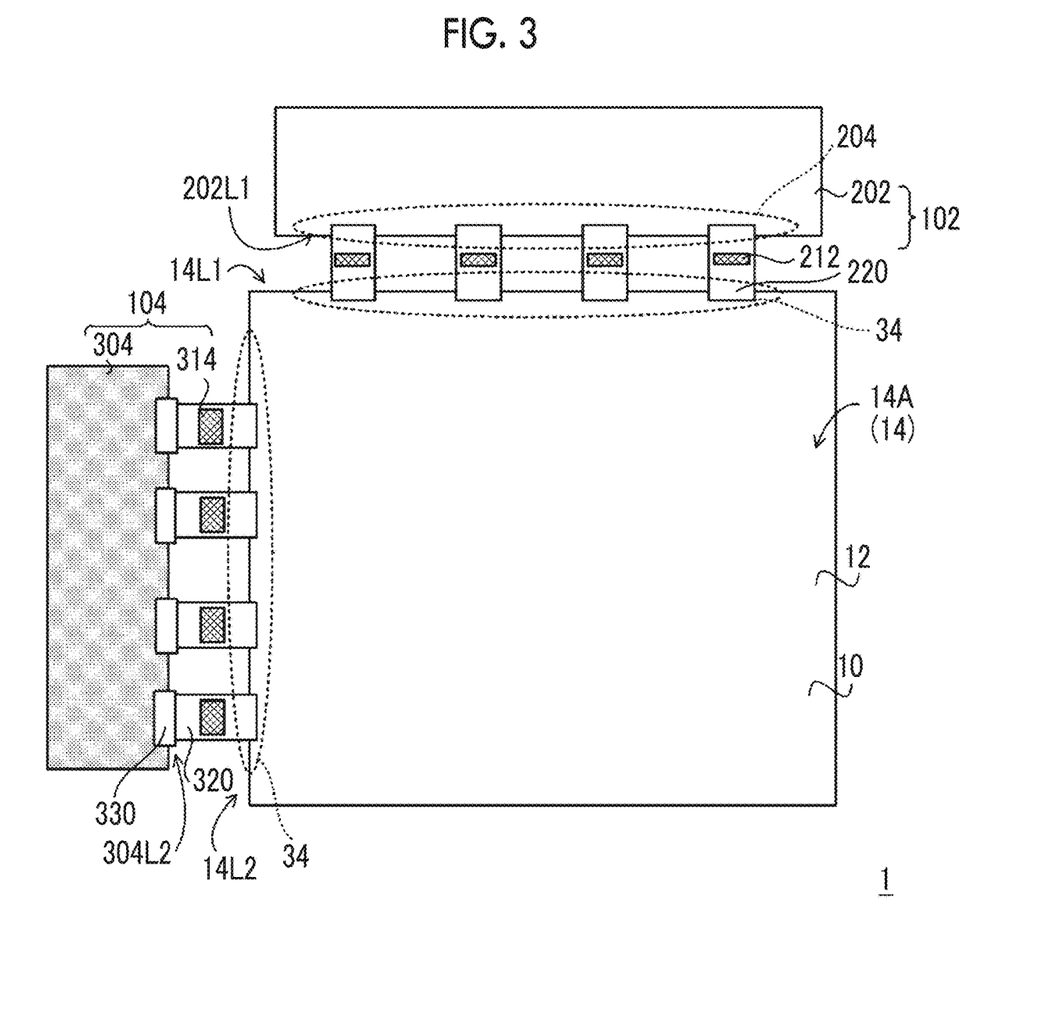
FIG. 3 is a plan view of one example of the radiation image capturing apparatus of the first exemplary embodiment seen from a side of a first surface of a base material.

Next, connection between the radiation detector 10 of the present exemplary embodiment and the driving unit 102 and the signal processing unit 104 will be described in detail. FIG. 3 illustrates a plan view in which one example of a state where the driving unit 102 and the signal processing unit 104 are connected to the radiation detector 10 of the present exemplary embodiment is seen from the first surface 14A side of the base material 14.

As illustrated in FIG. 3, flexible (having flexibility) cables 220 and cables 320 are electrically connected to terminals (not illustrated) disposed in the terminal region 34 of the base material 14 of the radiation detector 10. In the present exemplary embodiment, connection related to a component referred to as a "cable" including the cables 220 and the cables 320 means an electrical connection unless otherwise specified. The cables 220 and the cables 320 include signal lines (not illustrated) consisting of conductors and are electrically connected by connecting the signal lines to the terminals. The cables 220 of the present exemplary embodiment are one example of a first cable according to the embodiment of the present disclosure, and the cables 320 of the present exemplary embodiment are one example of a second cable according to the embodiment of the present disclosure. Hereinafter, in a case where the "cable" is referred to, the cable is flexible (having flexibility).

FIG. 3 illustrates a plan view in which one example of a state where the cables 220 and the cables 320 are connected to the terminal region 34 of the radiation detector 10 of the present exemplary embodiment is seen from the first surface 14A side of the base material 14. As illustrated in FIG. 3, in the present exemplary embodiment, the terminal region 34 is disposed in each of an outer edge portion 14L1 and an outer edge portion 14L2 of the radiation detector 10 having a rectangular shape. A side corresponding to the outer edge portion 14L1 and a side corresponding to the outer edge portion 14L2 are two sides adjacent to each other in the radiation detector 10. In other words, the side corresponding to the outer edge portion 14L1 and the side corresponding to the outer edge portion 14L2 in the radiation detector 10 intersect. The side corresponding to the outer edge portion 14L1 of the present exemplary embodiment is one example of a first side according to the embodiment of the present disclosure, and the side corresponding to the outer edge portion 14L2 of the present exemplary embodiment is one example of a second side according to the embodiment of the present disclosure.

In the outer edge portion 14L1, one end of a plurality of (in FIG. 3, four) cables 220 is connected to the terminals (not illustrated) of the terminal region 34 by thermocompression. The cables 220 have a function of connecting the driving unit 102 to the scanning wire 26 (refer to FIG. 1). A plurality of signal lines (not illustrated) included in the cables 220 are connected to the scanning wire 26 (refer to FIG. 1) of the sensor substrate 12 through the terminals of the terminal region 34.

The other end of the cables 220 is connected to terminals (not illustrated) disposed in a terminal region 204 of an outer edge portion 202L1 of a driving substrate 202 by thermocompression. A plurality of signal lines (not illustrated) included in the cables 220 are connected to circuits, elements, and the like mounted in the driving substrate 202 through the terminals of the terminal region 204. The driving substrate 202 of the present exemplary embodiment is one example of a first circuit substrate according to the present disclosure, and the circuits and the elements mounted in the driving substrate 202 of the present exemplary embodiment are one example of a first circuit unit according to the embodiment of the present disclosure.

Driving circuit units 212 are mounted in the cables 220. The driving circuit units 212 are connected to the plurality of signal lines (not illustrated) included in the cables 220.

In the present exemplary embodiment, the driving unit 102 is implemented by the circuits and the elements mounted in the driving substrate 202 and the driving circuit units 212. The driving circuit unit 212 is an integrated circuit (IC) that includes a circuit different from the circuits mounted in the driving substrate 202 among various circuits and elements implementing the driving unit 102.

The driving unit 102 and the scanning wire 26 are connected to each other by electrically connecting the sensor substrate 12 to the driving substrate 202 through the cables 220.

The driving substrate 202 of the present exemplary embodiment is a flexible printed circuit board (PCB) substrate and is a so-called flexible substrate.

In the outer edge portion 14L2, one end of a plurality (in FIG. 3, four) of cables 320 is connected to the terminals (not illustrated) of the terminal region 34 by thermocompression. A plurality of signal lines (not illustrated) included in the cables 320 are connected to the signal wire 24 (refer to FIG. 1) through the terminals of the terminal region 34. The cables 320 have a function of connecting the signal processing unit 104 to the signal wire 24 (refer to FIG. 1).

The other end of the cables 320 is electrically connected to connectors 330 disposed in an outer edge portion 304L2 of a signal processing substrate 304. The plurality of signal lines (not illustrated) included in the cables 320 are connected to circuits, elements, and the like mounted in the signal processing substrate 304 through the connectors 330. For example, connectors having a zero insertion force (ZIF) structure or connectors having a non-ZIF structure are exemplified as the connectors 330. The signal processing substrate 304 of the present exemplary embodiment is one example of a second circuit substrate according to the present disclosure, and the circuits and the elements mounted in the signal processing substrate 304 of the present exemplary embodiment are one example of a second circuit unit according to the embodiment of the present disclosure.

Signal processing circuit units 314 are mounted in the cables 320. The signal processing circuit units 314 are connected to the plurality of signal lines (not illustrated) included in the cables 320.

In the present exemplary embodiment, the signal processing unit 104 is implemented by the circuits and the elements mounted in the signal processing substrate 304 and the signal processing circuit units 314. The signal processing circuit units 314 are ICs that include circuits different from the circuits mounted in the signal processing substrate 304 among various circuits and elements implementing the signal processing unit 104.

The signal processing unit 104 and the signal wire 24 are connected to each other by electrically connecting the sensor substrate 12 to the signal processing substrate 304 through the cables 320 and the connectors 330.

The signal processing substrate 304 of the present exemplary embodiment is a non-flexible PWB substrate and is a so-called rigid substrate. Thus, the thickness of the signal processing substrate 304 is greater than the thickness of the driving substrate 202.

A method of manufacturing the radiation image capturing apparatus 1 illustrated in FIG. 1 and FIG. 3 will be described with reference to FIG. 4 and FIG. 5.

Figure 4:
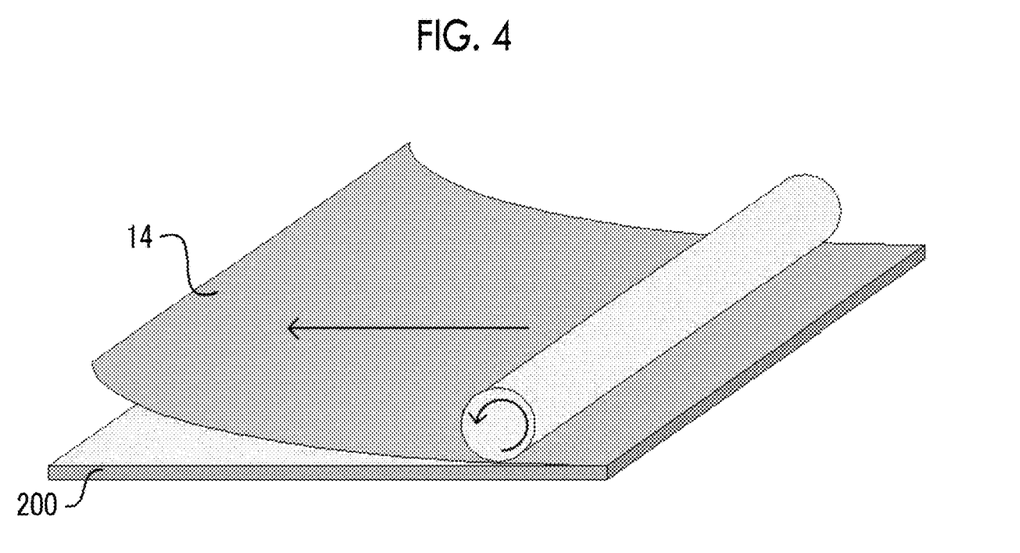
FIG. 4 is a descriptive diagram for describing one example of a method of manufacturing the radiation image capturing apparatus of the first exemplary embodiment.

First, as illustrated in FIG. 4, the base material 14 is formed in a support 200 such as a glass substrate having a greater thickness than the base material 14 through a stripping layer (not illustrated). In the case of forming the base material 14 using a lamination method, a sheet set as the base material 14 is bonded onto the support 200. The second surface 14B of the base material 14 is in contact with the stripping layer (not illustrated).

Furthermore, the pixels 16 are formed on the first surface 14A of the base material 14. In the present exemplary embodiment, for example, the pixels 16 are formed on the first surface 14A of the base material 14 through an undercoat (not illustrated) using SiN or the like.

Furthermore, the conversion layer 30 is formed on the pixels 16. In the present exemplary embodiment, the conversion layer 30 of CsI is directly formed on the sensor substrate 12 as columnar crystal using a vapor deposition method such as a vacuum evaporation method, a sputtering method, and a chemical vapor deposition (CVD) method. In this case, the side of the conversion layer 30 that is in contact with the pixels 16 is set as a base point side of the growth direction of the columnar crystal.

In a case where the conversion layer 30 of CsI is directly disposed on the sensor substrate 12 using the vapor deposition method, for example, a reflection layer (not illustrated) having a function of reflecting the light converted by the conversion layer 30 may be disposed on the surface of the conversion layer 30 on a side opposite to the side in contact with the sensor substrate 12. The reflection layer may directly disposed in the conversion layer 30 or may be disposed through a firm sticking layer or the like. It is preferable to use an organic-based material as the material of the reflection layer. For example, it is preferable to use at least one of white PET, $TiO_2$, $Al_2O_3$, foamed white PET, a polyester-based high reflection sheet, or specular reflection aluminum as the material. Particularly, it is preferable to use white PET as the material from the viewpoint of reflectance. The polyester-based high reflection sheet is a sheet (film) having a multilayer structure in which a plurality of thin polyester sheets are stacked.

In the case of using the scintillator of CsI as the conversion layer 30, the conversion layer 30 can be formed in the sensor substrate 12 using a different method from the present exemplary embodiment. For example, the conversion layer 30 may be formed in the sensor substrate 12 by preparing an aluminum plate or the like on which CsI is vapor-deposited using the vapor deposition method and bonding the side of CsI not in contact with the aluminum plate to the pixels 16 of the sensor substrate 12 using an adhesive sheet or the like. In this case, it is preferable that the entire conversion layer 30 including the aluminum plate in a state of being covered with a protective film is bonded to the pixels 16 of the sensor substrate 12. In this case, the side of the conversion layer 30 that is in contact with the pixels 16 is set as a distal end side of the growth direction of the columnar crystal.

In addition, unlike the radiation detector 10 of the present exemplary embodiment, $Gd_2O_2S:Tb$ (GOS) or the like may be used as the conversion layer 30 instead of CsI. In this case, for example, the conversion layer 30 can be formed in the sensor substrate 12 by preparing bonding of a sheet obtained by dispersing GOS in a binder of resin or the like to a support formed by white PET or the like using an adhesive layer or the like, and bonding a side of the GOS to which the support is not bonded to the pixels 16 of the sensor substrate 12 using an adhesive sheet or the like. The case of using CsI in the conversion layer 30 has higher efficiency of conversion from the radiation to the visible light than the case of using GOS.

Furthermore, the plurality of signal lines (not illustrated) included in the cables 220 are electrically connected to the scanning wire 26 (refer to FIG. 1) of the sensor substrate 12 by connecting the cables 220 to the terminals (not illustrated) of the terminal region 34 (refer to FIGS. 2 and 3) of the sensor substrate 12 by thermocompression. In addition, the plurality of signal lines (not illustrated) included in the cables 320 are electrically connected to the signal wire 24 (refer to FIG. 1) of the sensor substrate 12 by connecting the terminals (not illustrated) of the terminal region 34 (refer to FIGS. 2 and 3) of the sensor substrate 12 to the cables 320 by thermocompression.

Furthermore, the plurality of signal lines (not illustrated) included in the cables 220 are electrically connected to the circuits, the elements, and the like mounted in the driving substrate 202 by connecting the cables 220 to the terminals (not illustrated) of the terminal region 204 (refer to FIG. 3) of the driving substrate 202 by thermocompression.

Figure 5:
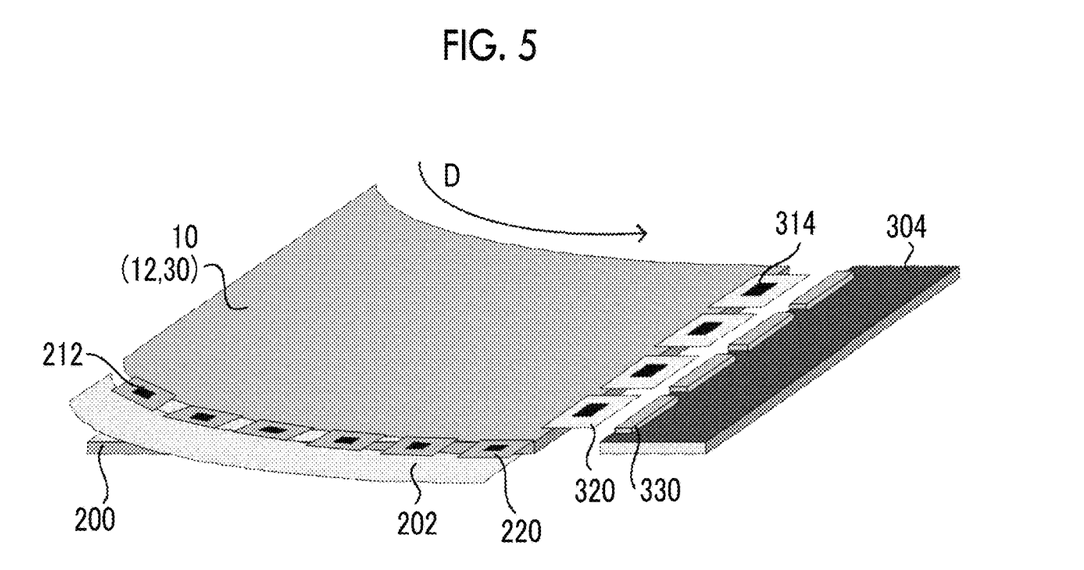
FIG. 5 is a descriptive diagram for describing one example of the method of manufacturing the radiation image capturing apparatus of the first exemplary embodiment.

Then, the radiation detector 10 is stripped from the support 200 as illustrated in FIG. 5. In the case of performing stripping by mechanical stripping, in one example illustrated in FIG. 5, the radiation image capturing apparatus 1 is obtained by performing mechanical stripping by setting the side facing the side to which the cables 320 are connected in the sensor substrate 12 as the starting point of stripping and gradually peeling the sensor substrate 12 from the support 200 in a direction of arrow D illustrated in FIG. 5 from the side set as the starting point to the side to which the cables 320 are connected.

In performing mechanical stripping, in a different case from the radiation image capturing apparatus 1 of the present exemplary embodiment, that is, in a case where the driving substrate 202 is the rigid substrate unlike the radiation image capturing apparatus 1 illustrated in FIG. 3 and FIG. 5, it is difficult to strip the sensor substrate 12 from the support 200 since the rigid substrate is less bent than the flexible substrate is. In addition, in the case of bending the driving substrate 202 that is the rigid substrate, the circuits, the elements, and the like mounted in the driving substrate 202 may be damaged.

Meanwhile, in the radiation image capturing apparatus 1 of the present exemplary embodiment, the driving substrate 202 is the flexible substrate as illustrated in FIG. 4 and FIG. 5 and thus, is easily bent in accordance with bending of the sensor substrate 12. Accordingly, the sensor substrate 12 is easily stripped from the support 200, and damage to the circuits, the elements, and the like mounted in the driving substrate 202 is suppressed.

In the present exemplary embodiment, furthermore, after the sensor substrate 12 is stripped from the support 200, the cables 320 of the radiation detector 10 are electrically connected to the connectors 330 of the signal processing substrate 304. The present disclosure is not limited to the present exemplary embodiment. The mechanical stripping may be performed after the cables 320 of the radiation detector 10 are electrically connected to the connectors 330 of the signal processing substrate 304. Even in this case, the side set as the base point to which the cables 320 are connected is almost not bent. Thus, the above problem does not arise unlike the case of the driving substrate 202.

Second Exemplary Embodiment

Figure 6:
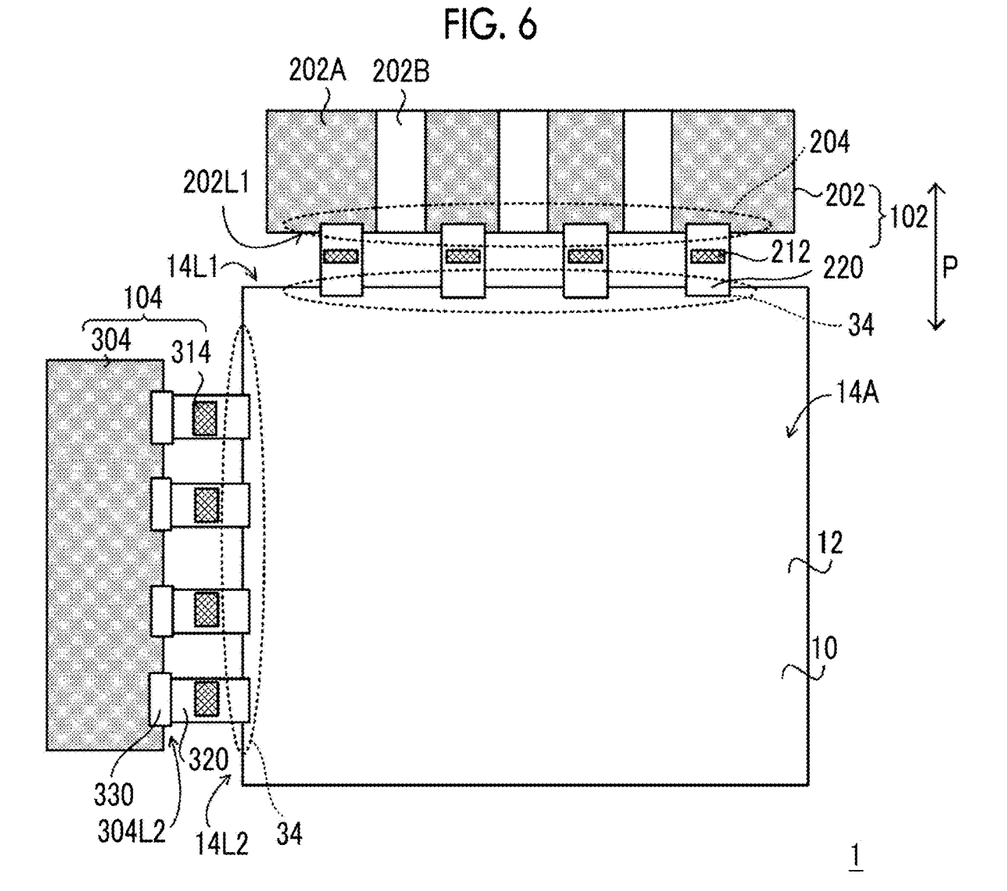
FIG. 6 is a plan view of one example of a radiation image capturing apparatus of a second exemplary embodiment seen from a side of a first surface of a base material.

FIG. 6 illustrates a plan view in which one example of the radiation image capturing apparatus 1 of the present exemplary embodiment is seen from the first surface 14A side of the base material 14.

As illustrated in FIG. 6, in the radiation image capturing apparatus 1 of the present exemplary embodiment, the driving substrate 202 is different from the driving substrate 202 (refer to FIG. 3) of the radiation image capturing apparatus 1 of the first exemplary embodiment.

As illustrated in FIG. 6, the driving substrate 202 of the present exemplary embodiment has non-flexible regions 202A and flexible regions 202B lined up in a direction intersecting with a connection direction (refer to arrow P in FIG. 6) in which the sensor substrate 12, the cables 220, and the driving substrate 202 are connected.

The non-flexible regions 202A are so-called rigid substrates like the signal processing substrate 304. Meanwhile, the flexible regions 202B are so-called flexible substrates like the driving substrate 202 of the first exemplary embodiment. A so-called rigid-flexible substrate can be applied as a substrate having the non-flexible regions 202A and the flexible regions 202B.

Figure 7:
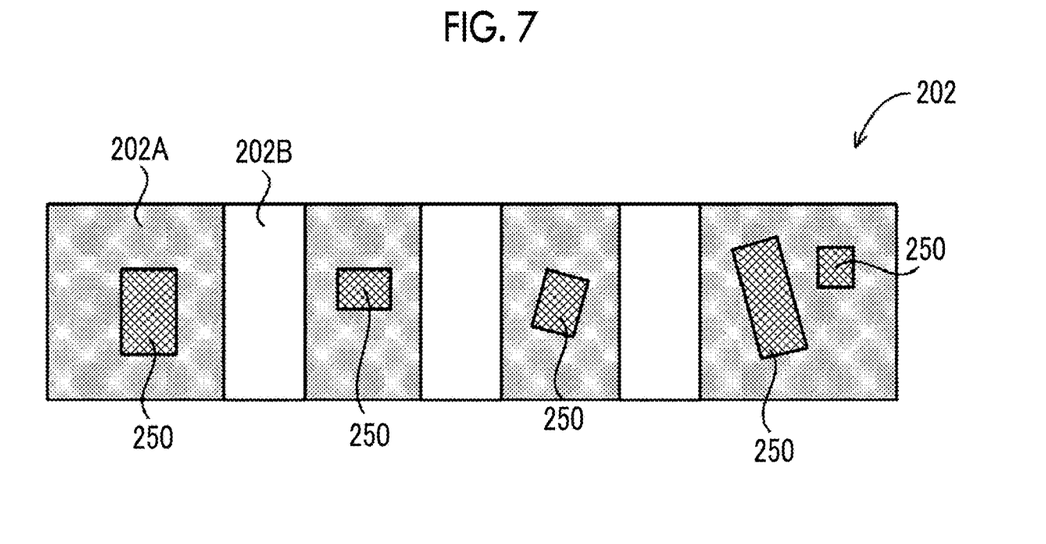
FIG. 7 is a descriptive diagram for describing a state where a driving component is mounted on a driving substrate of the second exemplary embodiment.

It is preferable that circuits and elements (hereinafter, referred to as "driving components") 250 mounted in the driving substrate 202 are mounted in the non-flexible regions 202A as in one example illustrated in FIG. 7. In addition, it is preferable that the driving components 250 are not mounted along boundaries between the non-flexible regions 202A and the flexible regions 202B.

In the radiation image capturing apparatus 1 of the present exemplary embodiment, even in a case where a part of the driving substrate 202 has the non-flexible regions 202A, the driving substrate 202 is easily bent due to the flexible regions 202B in a case where the radiation detector 10 is bent as in the case of mechanically stripping the radiation detector 10 from the support 200. Meanwhile, the part of the non-flexible regions 202A is not easily bent. Thus, in the case of bending the driving substrate 202, an effect exerted on the driving components 250 mounted in the non-flexible regions 202A can be reduced.

In addition, the thickness of the non-flexible regions 202A is generally greater than the thickness of the flexible regions 202B. By mounting the driving components 250 in a thick region, signal lines, components, or the like can be arranged to be spaced from each other in a thickness direction of the region (flexible regions 202B). Thus, electrical interference such as interference in the driving components 250 from a power supply line can be suppressed. In the present exemplary embodiment, the "power supply line" is a signal line used for supplying a power supply voltage and includes a signal line supplying a ground potential.

Figure 8:
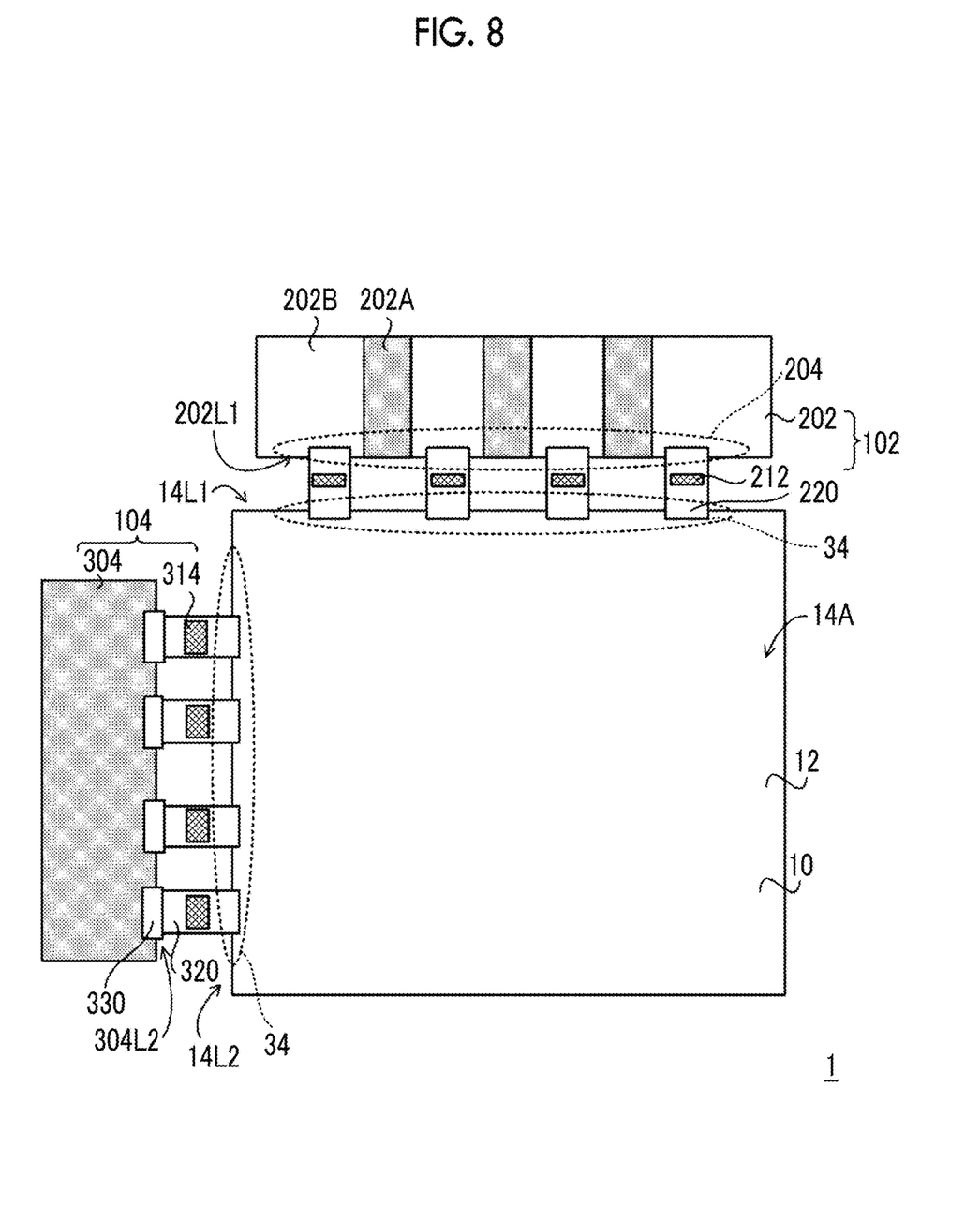
FIG. 8 is a plan view of another example of the radiation image capturing apparatus of the second exemplary embodiment seen from the side of the first surface of the base material.

In the driving substrate 202, the size and the number of each of the non-flexible regions 202A and the flexible regions 202B are not particularly limited. The arrangement, size, number, and the like of the driving components 250 mounted in the driving substrate 202 may be set in accordance with a manner of bending the sensor substrate 12 (the amount of bending and a curvature R). For example, the non-flexible regions 202A and the flexible regions 202B may be disposed as in one example illustrated in FIG. 8. In one example illustrated in FIG. 8, arrangement of the non-flexible regions 202A and the flexible regions 202B is reversed from the case of the driving substrate 202 illustrated in FIG. 6. Even in this case, the sensor substrate 12 can be easily bent. In addition, by mounting the driving components 250 in the non-flexible regions 202A, the effect exerted on the driving components 250 by bending the sensor substrate 12 can be reduced.

As described above, the radiation image capturing apparatus 1 of each exemplary embodiment comprises the sensor substrate 12 including the flexible base material 14 and the plurality of pixels 16 accumulating electric charges generated in accordance with the radiation, the flexible cables 220 of which one end is electrically connected to the sensor substrate 12, and the flexible driving substrate 202 that is electrically connected to the other end of the cables 220 and in which a circuit unit of the driving unit 102 driven in the case of reading out the electric charges accumulated in the plurality of pixels 16 is mounted.

In the radiation image capturing apparatus 1 of each exemplary embodiment, the flexible driving substrate 202 is connected to the sensor substrate 12 including the flexible base material through the flexible cables 220. Accordingly, in the radiation image capturing apparatus 1 of each exemplary embodiment, the effect exerted on the driving components 250 in a case where the sensor substrate 12 is bent in a state where the driving substrate 202 is electrically connected to the sensor substrate 12 through the cables 220 can be suppressed.

Particularly, in the case of applying the lamination method as the method of manufacturing the radiation image capturing apparatus 1, the sensor substrate 12 may be mechanically stripped from the support 200 in a state where the cables 220 and 320 and the driving substrate 202 are connected to the sensor substrate 12. In this case, the driving substrate 202 is bent in accordance with bending of the sensor substrate 12 in the case of stripping the sensor substrate 12 from the support 200. However, the effect exerted on the driving components 250 can be suppressed. In addition, according to the radiation image capturing apparatus 1 of each exemplary embodiment, the sensor substrate 12 is easily bent. Thus, the sensor substrate 12 can be easily stripped from the support 200.

Figure 9:
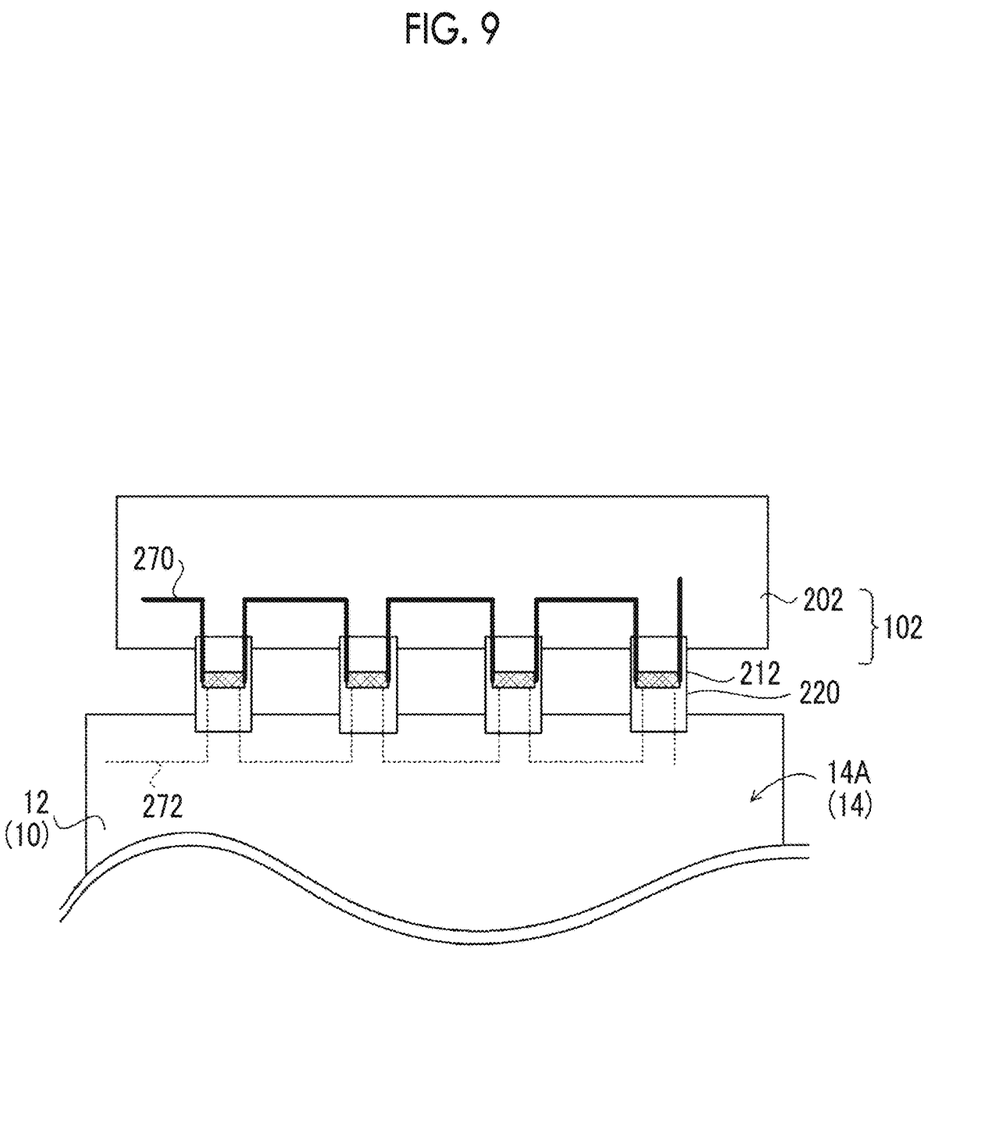
FIG. 9 is a descriptive diagram for describing one example of wires of a power supply line and a signal line for driving circuit units of the first and second exemplary embodiments.

In the radiation image capturing apparatus 1 of each exemplary embodiment, as in one example illustrated in FIG. 9, it is preferable that a power supply line 270 supplying power of the power supply for driving the driving circuit unit 212 is disposed in the driving substrate 202 and the cables 220 since the thickness of the base material 14 is relatively small. In other words, it is preferable that the power supply line 270 is not disposed in the sensor substrate 12. In addition, it is preferable that a signal line 272 through which a signal for driving the driving circuit unit 212 flows is disposed in the sensor substrate 12 and the cables 220.

The present disclosure is not limited to the radiation image capturing apparatus 1 of each exemplary embodiment. Which of at least one of the driving substrate 202 or the signal processing substrate 304 is to be set as a substrate having flexibility may be set in accordance with a stripping direction in the mechanical stripping of the above manufacturing step. The circuits, the elements, and the like that are used in the signal processing unit 104 and mounted in the signal processing substrate 304 generally perform analog-based processing. Components performing analog-based processing tend to significantly receive electrical interference, in other words, an effect of noise. Thus, it is preferable that the circuits, the elements, and the like mounted in the signal processing substrate 304 are disposed in an environment where the effect of noise is not easily received. As described above, the thickness of the rigid substrate is generally greater than the thickness of the flexible substrate. Thus, in the rigid substrate, compared to the flexible substrate, it is possible to increase the distance between the components and the power supply line or the signal line generating noise or make the noise difficult to interfere by stabilizing potential by increasing the thickness of a power supply layer or a ground layer. Accordingly, as in each exemplary embodiment, it is preferable that the signal processing substrate 304 is the rigid substrate.

The driving components 250 mounted in the driving substrate 202 generally perform digital-based processing. Components performing digital-based processing tend to be more unlikely to receive electrical interference, in other words, the effect of noise, than analog-based components are. Thus, the thickness of the driving substrate 202 can be set to be less than the thickness of the signal processing substrate 304. Accordingly, as in each exemplary embodiment, it is preferable that the driving substrate 202 is set as the flexible substrate.

In the case of manufacturing the radiation image capturing apparatus 1 using the lamination method, the sensor substrate 12 can be mechanically stripped from the support 200 before the driving substrate 202 and the cables 220 are connected to the sensor substrate 12. In this case, the driving substrate 202 and the cables 220 are connected to the sensor substrate 12 after the sensor substrate 12 is stripped from the driving substrate 202. However, since the sensor substrate 12 has flexibility, it is difficult to connect the driving substrate 202 and the cables 220 to the terminals of the terminal region 34 in the sensor substrate 12 by thermocompression, and a positional shift easily occurs. Accordingly, as in each exemplary embodiment, it is preferable that the sensor substrate 12 is stripped from the support 200 after the driving substrate 202 and the cables 220 are connected to the sensor substrate 12.

In each exemplary embodiment, the cables 320 and the signal processing substrate 304 are electrically connected by connecting the cables 320 to the connectors 330 disposed in the signal processing substrate 304. Alternatively, electrical connection may be made by thermocompression without using the connectors 330. As described above, since the signal processing substrate 304 is the rigid substrate, the signal processing substrate 304 tends to have a greater weight than the flexible substrate and is stretched depending on the weight, and there is a concern that the cables 320 cause a positional shift in the case of connecting the cables 320 to the signal processing substrate 304 by thermocompression. Thus, as in the radiation image capturing apparatus 1 of each exemplary embodiment, the case of connecting the signal processing substrate 304 to the cables 320 using the connectors 330 results in easy reworking and thus, is preferred. The "reworking" refers to detaching the components and cables connected to the substrate and newly connecting the components and cables again due to a defect, a positional shift, or the like.

While the form of configuring the signal processing unit 104 with the signal processing circuit units 314 and the signal processing substrate 304 mounted in the cables 320 is described in each exemplary embodiment, the present disclosure is not particularly limited thereto. For example, the signal processing unit 104 may be mounted in the cables 320, and the control substrate 110 may be electrically connected to the cables 320 instead of the signal processing substrate 304.

While the aspect in which the pixels 16 are two-dimensionally arranged in a matrix form as illustrated in FIG. 1 is described in each exemplary embodiment, the present disclosure is not limited thereto. For example, one-dimensional arrangement may be used, or honeycomb arrangement may be used. The shape of the pixels is also not limited and may be a rectangular shape or a polygonal shape such as a hexagonal shape. Furthermore, the shape of the active area 15 is not limited.

The radiation detector 10 (radiation image capturing apparatus 1) of each exemplary embodiment may be applied to a so-called irradiation side sampling (ISS) method of arranging the sensor substrate 12 on a side of the conversion layer 30 on which the radiation is incident, in other words, arranging the sensor substrate 12 on a side irradiated with the radiation in the radiation detector 10. In addition, the radiation detector 10 may be applied to a so-called penetration side sampling (PSS) method of arranging the sensor substrate 12 on a side opposite to the side of the conversion layer 30 on which the radiation is incident, in other words, arranging the sensor substrate 12 on a side opposite to the side irradiated with the radiation in the radiation detector 10.

Besides, the configurations, manufacturing methods, and the like of the radiation image capturing apparatus 1, the radiation detector 10, and the like described in each exemplary embodiment are one example and can be changed depending on situations without departing from the gist of the present disclosure.

The entire disclosure of Japanese Patent Application No. 2018-058964 is incorporated in the present specification by reference.

All documents, patent applications, and technical standards disclosed in the present specification are incorporated in the present specification by reference to the same extent as in a case where each of the documents, patent applications, and technical standards is specifically and individually indicated to be incorporated herein by reference.

What is claimed is:

1. A radiation image capturing apparatus comprising:
    a sensor substrate including a flexible base material and a plurality of pixels accumulating electric charges generated in accordance with radiation;
    a flexible first cable of which one end is electrically connected to the sensor substrate; and
    a flexible first circuit substrate that is electrically connected to the other end of the first cable and in which a first circuit unit driven in a case of reading out the electric charges accumulated in the plurality of pixels is mounted, wherein
    the first circuit substrate includes a flexible region and a non-flexible region that are lined up in a direction intersecting with a connection direction in which the sensor substrate, the first cable, and the first circuit substrate are connected.

2. The radiation image capturing apparatus according to claim 1, wherein the first cable is connected to a first side of the sensor substrate, and
    the radiation image capturing apparatus further comprises:
    a flexible second cable of which one end is electrically connected to a second side intersecting with the first side of the sensor substrate; and
    a non-flexible second circuit substrate that is electrically connected to the other end of the second cable and in which a second circuit unit which is different from the first circuit unit and is driven in a case of reading out the electric charges accumulated in the plurality of pixels is mounted.

3. The radiation image capturing apparatus according to claim 2, wherein
    the second circuit unit includes a circuit of a signal processing unit into which an electric signal corresponding to the electric charges accumulated in the plurality of pixels is input and that generates and outputs image data corresponding to the input electric signal.

4. The radiation image capturing apparatus according to claim 3, wherein
    the second circuit substrate includes a connector to which the second cable is electrically connected.

5. The radiation image capturing apparatus according to claim 2, wherein
    the second circuit substrate includes a connector to which the second cable is electrically connected.

6. The radiation image capturing apparatus according to claim 5, wherein
    the first cable is electrically connected to the first circuit substrate by thermocompression.

7. The radiation image capturing apparatus according to claim 5, wherein
    the first cable is electrically connected to the sensor substrate by thermocompression.

8. The radiation image capturing apparatus according to claim 2, wherein
    the first cable is electrically connected to the first circuit substrate by thermocompression.

9. The radiation image capturing apparatus according to claim 2, wherein
    the first cable is electrically connected to the sensor substrate by thermocompression.

10. The radiation image capturing apparatus according to claim 1, wherein
    the first circuit unit includes a circuit of a driving unit that reads out the electric charges from the plurality of pixels.

11. The radiation image capturing apparatus according to claim 1, wherein
    the first circuit unit is mounted in the non-flexible region.

12. The radiation image capturing apparatus according to claim 1, wherein
    a circuit of a driving unit reading out the electric charges from the plurality of pixels is mounted in the first cable, and
    a power supply line supplying power of a power supply to the circuit of the driving unit is disposed in the first circuit substrate and the first cable.

13. The radiation image capturing apparatus according to claim 12, wherein
    the circuit of the driving unit reading out the electric charges from the plurality of pixels is mounted in the first cable, and
    a signal line through which a signal for driving the circuit of the driving unit flows is disposed in the sensor substrate and the first cable.

14. The radiation image capturing apparatus according to claim 12, wherein
    the first cable is electrically connected to the sensor substrate by thermocompression.

15. The radiation image capturing apparatus according to claim 1, wherein
    a circuit of a driving unit reading out the electric charges from the plurality of pixels is mounted in the first cable, and
    a power supply line supplying power of a power supply to the circuit of the driving unit is not disposed in the sensor substrate.

16. The radiation image capturing apparatus according to claim 15, wherein
    the circuit of the driving unit reading out the electric charges from the plurality of pixels is mounted in the first cable, and a signal line through which a signal for driving the circuit of the driving unit flows is disposed in the sensor substrate and the first cable.

17. The radiation image capturing apparatus according to claim 1, wherein
the first cable is electrically connected to the first circuit substrate by thermocompression.

18. The radiation image capturing apparatus according to claim 17, wherein
the first cable is electrically connected to the sensor substrate by thermocompression.

19. The radiation image capturing apparatus according to claim 1, wherein
the first cable is electrically connected to the sensor substrate by thermocompression.

* * * * *